(12) United States Patent
Jang et al.

(10) Patent No.: US 10,551,312 B2
(45) Date of Patent: Feb. 4, 2020

(54) OPTICAL SENSOR, AND APPARATUS AND METHOD FOR MEASURING ABSORBANCE USING THE SAME

(71) Applicant: SAMSUNG ELECTRONICS CO., LTD., Suwon-si (KR)

(72) Inventors: Hyeong Seok Jang, Seoul (KR); Jae Wook Shim, Yongin-si (KR); Hyun Seok Moon, Seoul (KR); Hyo Sun Hwang, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 16/221,926

(22) Filed: Dec. 17, 2018

(65) Prior Publication Data
US 2019/0204220 A1 Jul. 4, 2019

(30) Foreign Application Priority Data
Dec. 29, 2017 (KR) .......................... 10-2017-0184288

(51) Int. Cl.
| | | |
|---|---|---|
| *G01N 21/45* | (2006.01) | |
| *G01N 21/59* | (2006.01) | |
| *A61B 5/024* | (2006.01) | |
| *A61B 5/00* | (2006.01) | |
| *G01N 21/33* | (2006.01) | |
| *G01N 21/77* | (2006.01) | |

(52) U.S. Cl.
CPC ........... *G01N 21/59* (2013.01); *A61B 5/0071* (2013.01); *A61B 5/02427* (2013.01); *A61B 5/443* (2013.01); *G01N 21/33* (2013.01); *G01N 21/77* (2013.01)

(58) Field of Classification Search
CPC ........ G01N 21/59; G01N 21/33; G01N 21/77; A61B 5/0071; A61B 5/02427; A61B 5/443
USPC ...................................................... 356/435
See application file for complete search history.

(56) References Cited

U.S. PATENT DOCUMENTS

| | | | |
|---|---|---|---|
| 10,061,157 B2 * | 8/2018 | Lee | ................... G02F 1/133603 |
| 2003/0169421 A1 | 9/2003 | Ehbets | |
| 2011/0261355 A1 | 10/2011 | Hannel et al. | |

(Continued)

FOREIGN PATENT DOCUMENTS

| | | |
|---|---|---|
| EP | 1314972 A1 | 5/2003 |
| JP | 2003243716 A | 8/2003 |

(Continued)

OTHER PUBLICATIONS

Communication dated Apr. 1, 2019, issued by the European Patent Office in counterpart European Application No. 18248150.7.

*Primary Examiner* — Roy M Punnoose
(74) *Attorney, Agent, or Firm* — Sughrue Mion, PLLC

(57) ABSTRACT

An optical sensor includes light sources configured to emit light, a substrate on which the light sources are mounted, the substrate comprising holes in regions on which the light sources are mounted, and a first photodetector configured to receive a first light emitted from a front surface of each of the light sources, the first light being reflected or scattered from an object. The optical sensor further includes at least one second photodetector configured to receive a second light emitted from a rear surface of each of the light sources, the second light passing through the holes corresponding to the light sources.

22 Claims, 11 Drawing Sheets

(56) References Cited

U.S. PATENT DOCUMENTS

| | | | |
|---|---|---|---|
| 2012/0150047 A1* | 6/2012 | Terumoto | A61B 5/02427 600/479 |
| 2015/0177141 A1 | 6/2015 | Yeo et al. | |
| 2015/0223749 A1 | 8/2015 | Park et al. | |
| 2016/0089088 A1 | 3/2016 | Kim et al. | |
| 2016/0161418 A1 | 6/2016 | Yeo | |
| 2016/0169800 A1 | 6/2016 | Deguchi et al. | |
| 2016/0206251 A1 | 7/2016 | Kwon et al. | |
| 2016/0273720 A1* | 9/2016 | Livesay | H01L 33/641 |

FOREIGN PATENT DOCUMENTS

| | | |
|---|---|---|
| JP | 4887251 B2 | 2/2012 |
| JP | 5012411 B2 | 8/2012 |
| JP | 2015-152601 A | 8/2015 |
| KR | 10-2009-0053500 A | 5/2009 |
| KR | 10-2009-0088667 A | 8/2009 |
| KR | 10-2016-0037576 A | 4/2016 |
| KR | 10-1737377 B1 | 5/2017 |
| WO | 2010060915 A2 | 6/2010 |
| WO | 2010/082852 A1 | 7/2010 |
| WO | 2011040467 A1 | 4/2011 |
| WO | 2014009139 A1 | 1/2014 |

* cited by examiner

OPTICAL SENSOR, AND APPARATUS AND METHOD FOR MEASURING ABSORBANCE USING THE SAME

CROSS-REFERENCE TO RELATED APPLICATION(S)

This application claims priority from Korean Patent Application No. 10-2017-0184288, filed on Dec. 29, 2017, in the Korean Intellectual Property Office, the entire disclosure of which is incorporated herein by reference for all purposes.

BACKGROUND

1. Field

Apparatuses and methods consistent with embodiments related to optical sensors and absorbance measurement.

2. Description of the Related Art

Absorbance may be used to analyze samples in various applications such as environment monitoring, food inspection, and medical diagnosis. Bio-information may be obtained by continuously measuring skin absorbance with a small spectrometer and analyzing the measurements.

When light is emitted onto skin by using an LED to measure the skin absorbance, a quantity of light emitted by the LED is changed due to an effect of skin temperature. Such change in the light quantity of LED leads to an error in measured values of skin absorbance, which may reduce accuracy when information is obtained from a small measured value (e.g., when a blood glucose level is estimated based on a skin spectrum).

SUMMARY

Embodiments may address at least the above problems and/or disadvantages and other disadvantages not described above. Also, the embodiments are not required to overcome the disadvantages described above, and may not overcome any of the problems described above.

According to embodiments, there is provided an optical sensor including light sources configured to emit light, a substrate on which the light sources are mounted, the substrate comprising holes in regions on which the light sources are mounted, and a first photodetector configured to receive a first light emitted from a front surface of each of the light sources, the first light being reflected or scattered from an object. The apparatus further includes at least one second photodetector configured to receive a second light emitted from a rear surface of each of the light sources, the second light passing through the holes corresponding to the light sources.

The light sources may be further configured to emit light of different wavelengths.

A number of the at least one second photodetectors may be equal to a number of the light sources, and the at least one second photodetector may correspond to the light sources.

A number of the at least one second photodetector may be less than a number of the light sources.

A number of the at least one second photodetector may be one.

The optical sensor may further include a light collector disposed between the substrate and the at least one second photodetector, and configured to collect the second light passed through the holes.

The light collector may include any one or any combination of a waveguide, a condensing lens, a reflection mirror, and a grating.

According to embodiments, there is provided an apparatus for measuring absorbance, the apparatus including an optical sensor configured to receive a first light and a second light. The first light may be reflected or scattered from an object, and the second light may pass through holes of a substrate. The optical sensor is further configured to measure a first light quantity of the first light, and measure a second light quantity of the second light. The apparatus further includes a processor configured to calculate an absorbance of the object, based on the first light quantity of the first light and the second light quantity of the second light.

The optical sensor may include light sources configured to emit light, the substrate on which the light sources are mounted, the substrate comprising the holes in regions on which the light sources are mounted, a first photodetector configured to receive the first light emitted from a front surface of each of the light sources, the first light being reflected or scattered from the object, and measure the first light quantity of the first light, and at least one second photodetector configured to receive the second light emitted from a rear surface of each of the light sources, the second light passing through the holes corresponding to the light sources, and measure the second light quantity of the second light.

The optical sensor may further include a light collector disposed between the substrate and the at least one second photodetector, and configured to collect the second light passed through the holes.

The light collector may include any one or any combination of a waveguide, a condensing lens, a reflection mirror, and a grating.

The processor may be further configured to calibrate the first light quantity of the first light, based on a change in the second light quantity of the second light, and calculate the absorbance of the object, using the first light quantity that is calibrated.

The processor may be further configured to calibrate the first light quantity of the first light, using a light quantity calibration equation defining a relationship between the change in the second light quantity of the second light and the first light quantity of the first light.

The processor may be further configured to determine whether the light sources are stabilized, and based on the light sources being determined to be stabilized, calculate the absorbance of the object, based on the first light quantity of the first light and the second light quantity of the second light.

The processor may be further configured to determine whether the light sources are stabilized based on any one or any combination of a coefficient of variation of the second light quantity of the second light, a degree of wavelength shift of the light sources, and a preset time.

According to embodiments, there is provided a method of measuring absorbance, the method comprising receiving a first light that is emitted from a front surface of a light source and is reflected or scattered from an object, measuring a first light quantity of the first light, receiving a second light that is emitted from a rear surface of the light source and passes through a hole of a substrate on which the light source is mounted, measuring a second light quantity of the second light, and calculating absorbance of the object, based on the first light quantity of the first light and the second light quantity of the second light.

The calculating the absorbance of the object may include calibrating the first light quantity of the first light, based on a change in the second light quantity of the second light, and calculating the absorbance of the object, using the first light quantity that is calibrated.

The calibrating the first light quantity of the first light may include calibrating the first light quantity of the first light, using a light quantity calibration equation defining a relationship between the change in the second light quantity of the second light and the first light quantity of the first light.

The method may further include determining whether the light source is stabilized.

The determining whether the light source is stabilized may include determining whether the light source is stabilized, based on any one or any combination of a coefficient of variation of the second light quantity of the second light, a degree of wavelength shift of the light source, and a preset time.

The calculating of absorbance of the object may include, based on the light source being determined to be stabilized, calculating the absorbance of the object, based on the first light quantity of the first light and the second light quantity of the second light.

According to embodiments, there is provided an optical sensor comprising light sources, each of the light sources being configured to emit a first light from a first surface, and emit a second light from a second surface opposite to the first surface, a first substrate comprising holes on which the second surface of each of the light sources is respectively disposed, a first photodetector configured to receive the first light that is emitted from each of the light sources and that is reflected or scattered from an object, one or more second photodetectors configured to receive the second light that is emitted from each of the light sources and that passes through each of the holes respectively corresponding to the light sources, and a second substrate on which the one or more second photodetectors are mounted.

BRIEF DESCRIPTION OF THE DRAWINGS

The above and/or other aspects will be more apparent by describing embodiments with reference to the accompanying drawings.

Figure 1A:
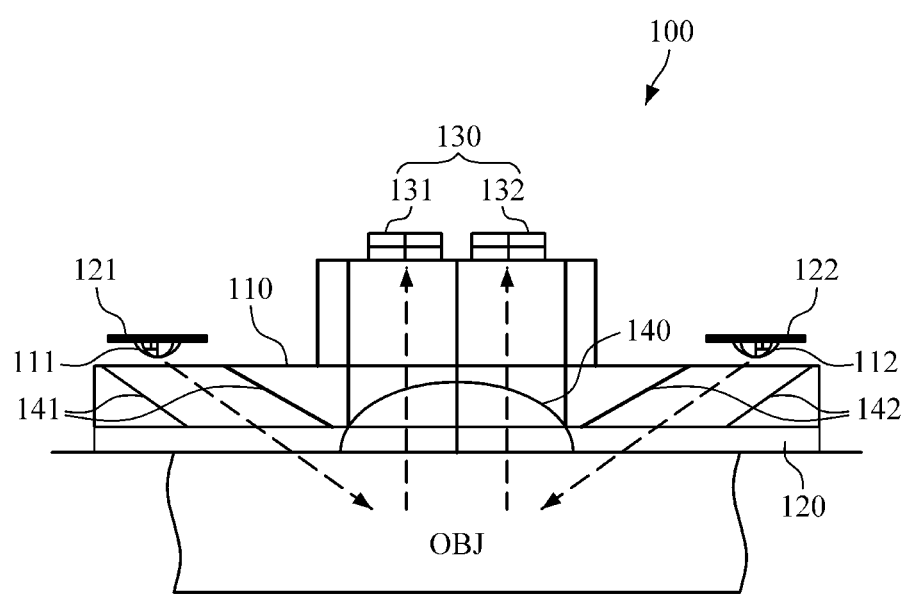
FIG. 1A is a diagram schematically illustrating a structure of an optical sensor according to an embodiment.

Throughout the drawings and the detailed description, unless otherwise described, the same drawing reference numerals will be understood to refer to the same elements, features, and structures. The relative size and depiction of these elements may be exaggerated for clarity, illustration, and/or convenience.

DETAILED DESCRIPTION

Embodiments are described in greater detail below with reference to the accompanying drawings.

Hereinafter, embodiments of the disclosure will be described in detail with reference to the accompanying drawings. In the drawings, the same reference symbols refer to same parts although illustrated in other drawings. In the following description, a detailed description of known functions and configurations incorporated herein will be omitted when it may obscure the subject matter. Also, well-known functions or constructions may not be described in detail because they would obscure the description with unnecessary detail.

As used herein, the term "and/or" includes any and all combinations of one or more of the associated listed items. Expressions such as "at least one of," when preceding a list of elements, modify the entire list of elements and do not modify the individual elements of the list.

Process steps described herein may be performed differently from a specified order, unless a specified order is clearly stated in the context of the disclosure. That is, each step may be performed in a specified order, at substantially the same time, or in a reverse order.

Further, the terms used throughout this specification are defined in consideration of the functions according to embodiments, and can be varied according to a purpose of a user or manager, or precedent and so on. Therefore, definitions of the terms may be made on the basis of the overall context.

The terms first, second, etc. may be used herein to describe various elements, these elements may not be limited by these terms. These terms are only used to distinguish one element from another. References to singular may include plural unless expressly stated otherwise. In the present specification, the terms, such as 'including' or 'having,' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Further, components that will be described in the specification are discriminated according to functions performed by the components. That is, two or more components which will be described later may be integrated into a single component. Furthermore, a single component which will be explained later can be separated into two or more components. Moreover, each component which will be described can additionally perform some or all of a function executed by another component in addition to the main function thereof. Some or all of the main function of each component which will be explained can be carried out by another component. Each component may be implemented as hardware, software, and/or a combination of both.

Descriptions of embodiments below may not be understood as limiting the scope of right, but those easily inferred by one of ordinary skill in the art may be understood as belonging to the scope or right of the embodiments. Hereinafter, embodiments will be described in detail by referring to the accompanying drawings for the purpose of describing examples only.

Figure 1B:
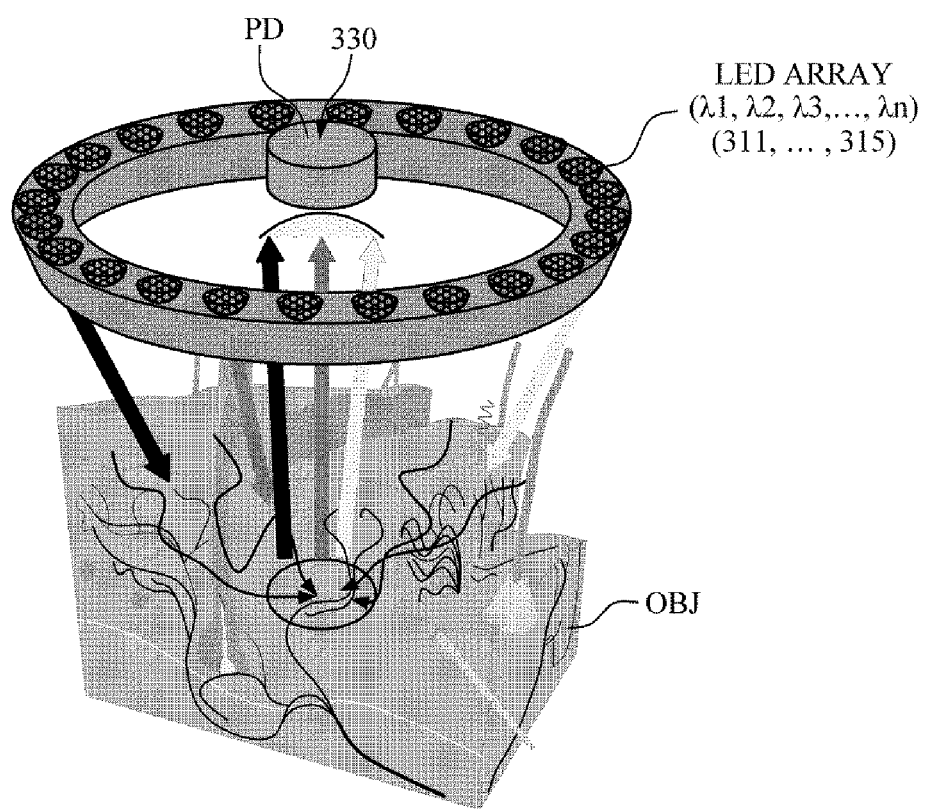
FIG. 1B is a diagram illustrating an example of arrangement of light sources and a photodetector of an optical sensor according to an embodiment.

FIG. 1A is a diagram schematically illustrating a structure of an optical sensor according to an embodiment. FIG. 1B is a diagram illustrating an example of arrangement of light sources and a photodetector of an optical sensor according to an embodiment.

Referring to FIG. 1A, the optical sensor 100 includes a housing 110 in which light sources 111 and 112, photodetectors 131 and 132, and the like may be mounted. Although FIG. 1A illustrates an example where the light sources 111 and 112 and the photodetectors 131 and 132 are respectively two in number, this is an example and the number thereof is not limited.

Further, the optical sensor 100 may include a cover 120 formed at the bottom thereof where the optical sensor 100 comes into contact with an object OBJ. In this case, the cover 120 may be made of anti-reflection coated glass.

In addition, the optical sensor 100 may further include direction adjusters 141 and 142 which are mounted in the housing 110 and adjust the direction of light emitted by the light sources 111 and 112. The direction adjusters 141 and 142 may be optical mirrors and may be configured to adjust the direction of light, emitted by the light sources 111 and 112, toward an object OBJ to be examined, e.g., the radial artery, veins, or capillaries in the wrist. The direction and angle of the direction adjuster 141 and 142 may be preset at the initial operation, but are not limited thereto and may be automatically adjusted according to a predetermined control signal.

Light, emitted by the light sources 111 and 112, enters into the object OBJ along a light path as indicated by an arrow, and is reflected or scattered from the object OBJ depending on tissue properties of the object OBJ to travel toward the photodetectors 131 and 132. Each of the photodetectors 131 and 132 detects light returning from the object OBJ. In this case, the optical sensor 100 may include a light concentrator 140 which concentrates light, reflected or scattered from the object OBJ, to be directed toward the photodetectors 131 and 132; and the light concentrator 140 may be an optical module such as an optical lens.

Further, the optical sensor 100 may include wavelength adjusters 121 and 122 which adjust wavelengths of the light sources 111 and 112 according to a predetermined control signal. The wavelength adjusters 121 and 122 may be adhered to one surface of the light sources 111 and 112. In this case, the wavelength adjusters 121 and 122 may be detachable from the respective light sources 111 and 112, or may be integrally formed therewith; and may be a temperature controlling member, such as a resistance heating element or a thermoelement, which controls temperature of the light sources 111 and 112.

The light sources 111 and 112 may be arranged on an outer periphery of the photodetectors 131 and 132 to surround the photodetectors 131 and 132. For example, the light sources 111 and 112 may be disposed in the form of a concentric circle centered on the photodetectors 131 and 132 to surround the photodetectors 131 and 132.

For example, as illustrated in FIG. 1B, the optical sensor 100 may include a photodiode PD formed at the center thereof, and an LED array having n number of LEDs disposed on an outer periphery of the photodiode PD in the form of a concentric circle centered on the photodiode PD. In this case, the LEDs may be preset to have different peak wavelengths $\lambda_1, \lambda_2, \lambda_3, \ldots,$ and $\lambda_n$.

Figure 2:
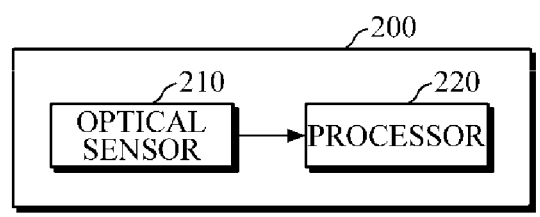
FIG. 2 is a block diagram illustrating an example of an apparatus for measuring absorbance according to a first embodiment.

FIG. 2 is a block diagram illustrating an example of an apparatus for measuring absorbance according to an embodiment. The apparatus depicted in FIG. 2 is an apparatus capable of measuring absorbance of an object, and may be embedded in an electronic device. In this case, examples of the electronic device may include a cellular phone, a smartphone, a tablet PC, a laptop computer, a personal digital assistant (PDA), a portable multimedia player (PMP), a navigation, an MP3 player, a digital camera, a wearable device, and the like. Examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, neither the electronic device nor the wearable device is limited to the listed examples.

Referring to FIG. 2, the apparatus 200 for measuring absorbance includes an optical sensor 210 and a processor 220.

The optical sensor 210 may receive light (hereinafter referred to as a first light) which is emitted from a front surface of each light source and is reflected and scattered from an object, and may measure a light quantity of the received first light. Further, the optical sensor 210 may receive light (hereinafter referred to as a second light) which is emitted from a rear surface of each light source and passes through holes of a substrate where the light sources are mounted.

The processor 220 may process various signals related to operation of the apparatus 200 for measuring absorbance.

The processor 220 may control the optical sensor 210 to obtain light quantities of the first light and the second light, which have various wavelengths, according to a predetermined cycle or a user's request.

The processor 220 may determine whether light sources of the optical sensor 210 are stabilized. In one embodiment, the processor 220 may determine whether the light sources are stabilized by using a coefficient of variation of a light quantity of the second light, a degree of wavelength shift of the light sources, a preset time, and the like. For example, the processor 220 may determine the stability of the light sources in response to a coefficient of variation of a light quantity of the second light being less than or equal to a predetermined first threshold value, in response to a degree of wavelength shift of the light sources. The degree of wavelength shift of the light source may be calculated based on a light quantity of the second light, being less than or equal to a predetermined second threshold value, or in response to a lapse of time preset to operate the light sources.

Upon determining that the light sources are stabilized, the processor 220 may calculate absorbance of an object based on a light quantity of the first light and a light quantity of the second light.

In one embodiment, based on the light quantity of the second light, the processor 220 may estimate a light quantity (hereinafter referred to as an incident light quantity) which is emitted from a front surface of the light sources and is incident on an object. Based on the estimated incident light quantity and the light quantity of the first light, the processor 220 may calculate absorbance of the object. In this case, the processor 220 may use the following Equation 1.

$$A = -\log\left(\frac{I_1}{I_0}\right) = -\log\left(\frac{I_1}{\alpha I_2}\right) \qquad \text{[Equation 1]}$$

Herein, A denotes absorbance, $I_1$ denotes the light quantity of the first light, $I_0$ denotes the incident light quantity, $I_2$ denotes the light quantity of the second light, and α denotes a calibration factor, in which a may be obtained experimentally.

In another example, the processor 220 may calibrate the light quantity of the first light based on the light quantity of the second light, and may calculate absorbance of an object by using the calibrated light quantity of the first light. In this case, the processor 220 may use the following Equation 2 (hereinafter referred to as a light quantity calibration equation) and Equation 3.

$$I_{cal} = I_1 \times \frac{100}{100 + \beta} \quad \text{[Equation 2]}$$

$$A = -\log\left(\frac{I_{cal}}{I'_0}\right) \quad \text{[Equation 3]}$$

Herein, $I_{cal}$ denotes the calibrated light quantity of the first light, $I_1$ denotes the measured light quantity of the first light, β denotes a variation (expressed as a percentage %) in the light quantity of the second light compared to a previous quantity of the second light, and $I'_0$ denotes an initial value of the incident light quantity. In this case, the initial value of the incident light quantity may be obtained by measuring light reflected or scattered from a reference material (material having 99% diffuse reflection properties), or may be estimated from an initially measured light quantity of the second light.

Figure 3:
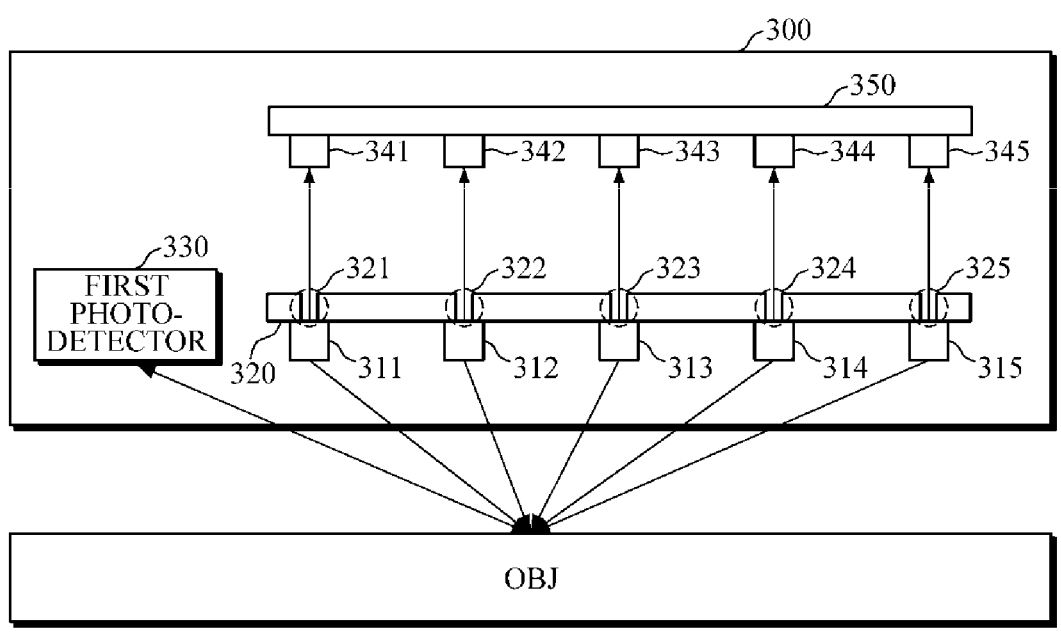
FIG. 3 is a diagram illustrating a structure of an optical sensor according to a first embodiment.

FIG. 3 is a diagram illustrating an example of a structure of an optical sensor. The optical sensor 300 of FIG. 3 is an embodiment of the optical sensor 210 of FIG. 2, and the number of light sources and second photodetectors of FIG. 3 is equal to the number of those in optical sensor 210 of FIG. 2. The optical sensor 300 of FIG. 3 may be configured based on the structure of the optical sensor 100 described above with reference to FIGS. 1A and 1B.

Referring to FIG. 3, the optical sensor 300 includes a plurality of light sources 311 to 315, substrates 320 and 350, a first photodetector 330, and a plurality of second photodetectors 341 to 345.

The light sources 311 to 315 may emit light of different wavelengths. For example, each of the light sources 311 to 315 may emit visible light or infrared light from a front surface or a rear surface. However, the wavelengths of light emitted from each of the light sources 311 to 315 are not limited thereto, and may vary depending on the type of measurement, the target to be analyzed, and the like. In one embodiment, the light sources 311 to 315 may include a light-emitting diode (LED), a laser diode, or the like, but this is an example and the light sources 311 and 315 are not limited thereto.

The light sources 311 to 315 may be mounted at the substrate 320, and holes 321 to 325 corresponding to each of the light sources 311 to 315 may be formed in a region of the substrate 320 where the light sources 311 to 315 are mounted.

The first photodetector 330 may receive a first light which is emitted from a front surface of each of the light sources 311 to 315 and is reflected or scattered from an object OBJ, and may measure a light quantity of the received first light. In one embodiment, the first photodetector 330 may include a photo diode, a photo transistor (PTr), a charge-coupled device (CCD), and the like. The first photodetector 330 is not necessarily a single device, but may be an array of a plurality of devices.

Further, as illustrated in FIG. 1B, the light sources 311 to 315 may be arranged on an outer periphery of the first photodetector 330 to surround the first photodetector 330.

The second photodetectors 341 to 345 shown in FIG. 3 may receive a second light which is emitted from a rear surface of the light sources 311 to 315 and passes through the holes 321 to 325 of the substrate 320, and may measure a light quantity of the received second light. In one embodiment, the second photodetectors 341 to 345 may include a photo diode, a photo transistor (PTr), a charge-coupled device (CCD), and the like.

In one embodiment, the second photodetectors 341 to 345 may correspond one-to-one with the light sources 311 to 315. For example, the second photodetector 341 corresponds one-to-one with the light source 311, the second photodetector 342 corresponds one-to-one with the light source 312, the second photodetector 343 corresponds one-to-one with the light source 313, the second photodetector 344 corresponds one-to-one with the light source 314, and the second photodetector 345 corresponds one-to-one with the light source 315. In this configuration the second photodetector 341 may receive the second light emitted from a rear surface of the light source 311 and passes through the hole 321; the second photodetector 342 may receive the second light emitted from a rear surface of the light source 312 and passes through the hole 322; the second photodetector 343 may receive the second light emitted from a rear surface of the light source 313 and passes through the hole 323; the second photodetector 344 may receive the second light emitted from a rear surface of the light source 314 and passes through the hole 324; and the second photodetector 345 may receive the second light emitted from a rear surface of the light source 315 and passes through the hole 325.

The plurality of second photodetectors 341 to 345 may be mounted to the substrate 350.

The optical sensor 300 may further include various optical elements so that light may be emitted onto a target object OBJ.

FIG. 3 illustrates an example where the optical sensor 300 includes five light sources, one first photodetector, and five second photodetectors, but this is an example. The number and arrangement of the light sources, the first photodetector, and the second photodetector may vary according to a purpose of use of the optical sensor 300 and the size and shape of an electronic device including the optical sensor 300.

Figure 4:
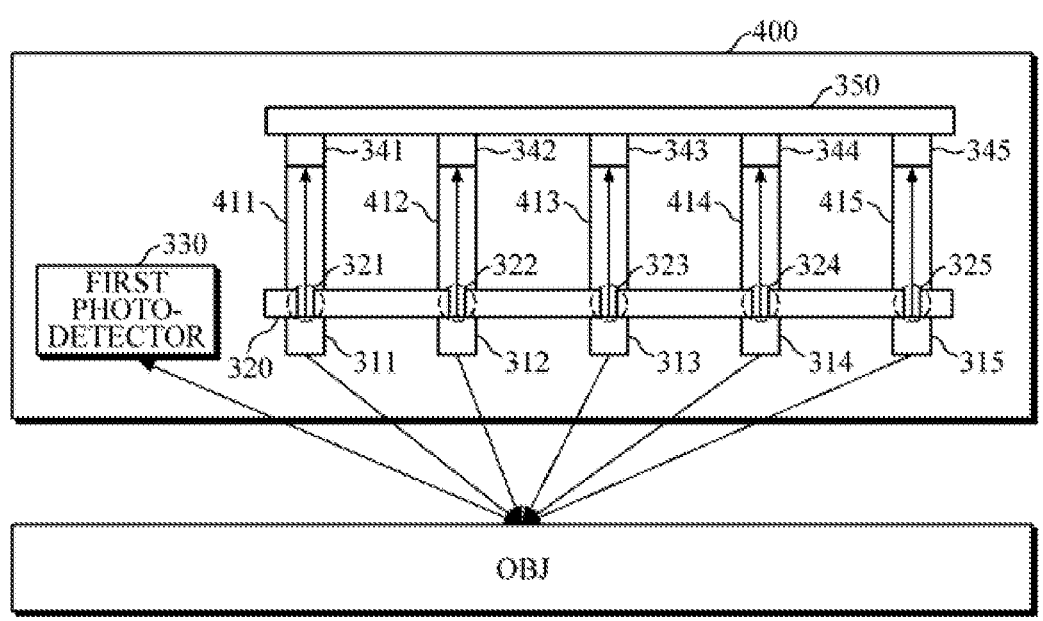
FIG. 4 is a diagram illustrating a structure of an optical sensor according to a second embodiment.

FIG. 4 is a diagram illustrating another example of a structure of an optical sensor. The optical sensor 400 of FIG. 4 may be an example of the optical sensor 210 of FIG. 2. The optical sensor 400 of FIG. 4 may be configured based on the structure of the optical sensor 100 described above with reference to FIGS. 1A and 1B.

Referring to FIGS. 3 and 4, the optical sensor 400 may further include a plurality of light collectors 411 to 415 as compared to the structure of the optical sensor 300.

The light collectors 411 to 415 my collect the second light which is emitted from a rear surface of each of the light sources 311 to 315 and passes through the holes 321 to 325. In one embodiment, the light collectors 411 to 415 may include a waveguide, a condensing lens, a reflection mirror, a grating, and the like.

Figure 5:
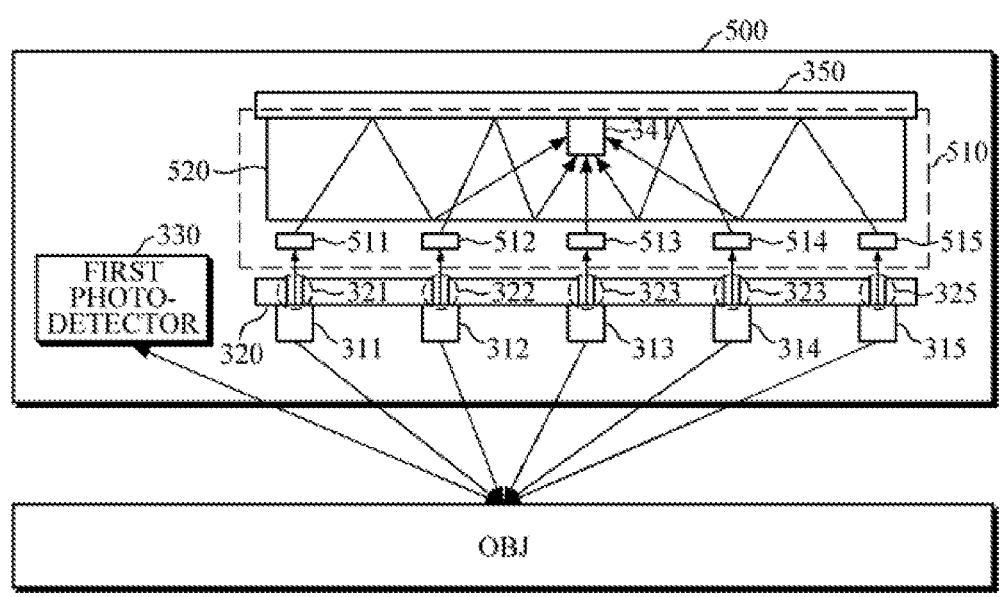
FIG. 5 is a diagram illustrating a structure of an optical sensor according to a third embodiment.

FIG. 5 is a diagram illustrating yet another example of a structure of an optical sensor. The optical sensor 500 of FIG. 5 is an example of the optical sensor 210 of FIG. 2, and includes a single second photodetector. The optical sensor 500 of FIG. 5 may be configured based on the structure of the optical sensor 100 described above with reference to FIGS. 1A and 1B.

Referring to FIG. 5, the optical sensor 500 includes a plurality of light sources 311 to 315, substrates 320 and 350, a first photodetector 330, a single second photodetector 341, and a light collector 510. Here, the plurality of light sources 311 to 315, the substrates 320 and 350, the first photodetector 330, and the second photodetector 341 are described above with reference to FIG. 3 such that detailed description thereof will be omitted.

The light collector 510 may collect the second light which is emitted from a rear surface of each of the light sources 311 to 315 and passes through the holes 321 to 325; and may include a plurality of gratings 511 to 515 and a waveguide 520 to enable the second photodetector 341 to receive the collected second light. Further, depending on embodiments, the light collector 510 may further include a reflection mirror, a condensing lens, and the like.

Figure 6:
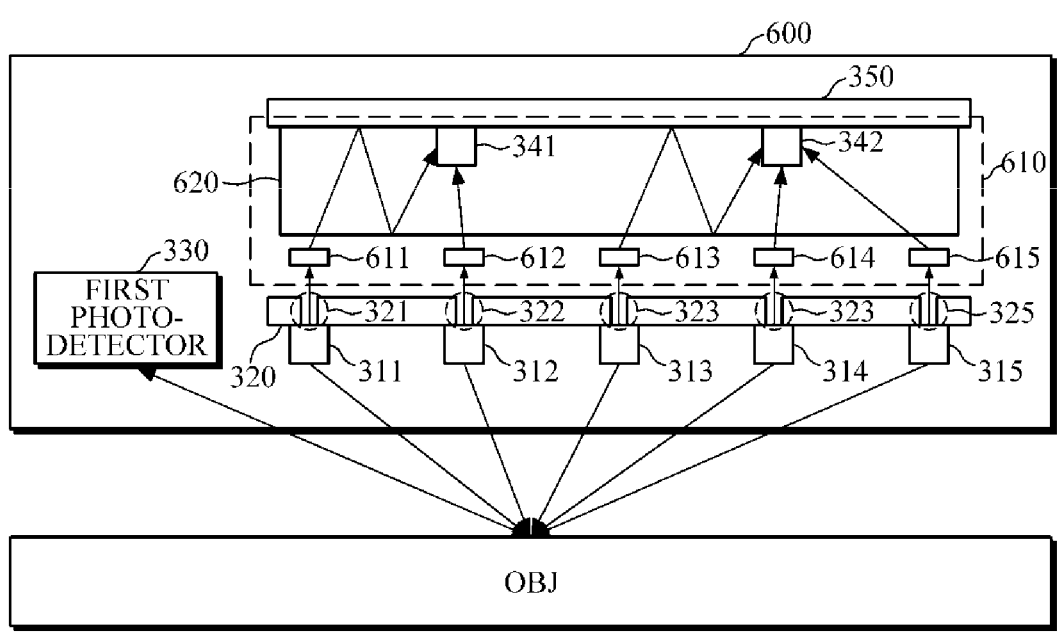
FIG. 6 is a diagram illustrating a structure of an optical sensor according to a fourth embodiment.

FIG. 6 is a diagram illustrating still another example of a structure of an optical sensor. The optical sensor 600 of FIG. 6 is an example of the optical sensor 210 of FIG. 2, and FIG. 6 illustrates an example where the number of photodetectors is less than the number of light sources. The optical sensor 600 of FIG. 6 may be configured based on the structure of the optical sensor 100 described above with reference to FIGS. 1A and 1B.

Referring to FIG. 6, the optical sensor 600 includes a plurality of light sources 311 to 315, substrates 320 and 350, a first photodetector 330, second photodetectors 341 and 342, and a light collector 610. Here, the plurality of light sources 311 to 315, the substrates 320 and 350, the first photodetector 330, and the second photodetectors 341 and 342 are described above with reference to FIG. 3 such that detailed description thereof will be omitted.

The light collector 610 may collect the second light which is emitted from a rear surface of each of the light sources 311 to 315 and passes through the holes 321 to 325; and may include a plurality of gratings 611 to 615 and a waveguide 620 to enable the second photodetector 341 or the second photodetector 342 to receive the collected second light. Further, depending on embodiments, the light collector 610 may further include a reflection mirror, a condensing lens, and the like.

Although FIG. 6 illustrates an example where the optical sensor 600 includes two second photodetectors, the second photodetector 341 receives the second light emitted by the light sources 311 and 312, and the second photodetector 342 receives the second light emitted by the light sources 313 to 315, this is an example. That is, the number and arrangement of the second photodetectors, and a corresponding relationship between the second photodetectors and the light sources may vary according to a purpose of use of the optical sensor 600 and the size and shape of an electronic device including the optical sensor 600.

Figure 7:
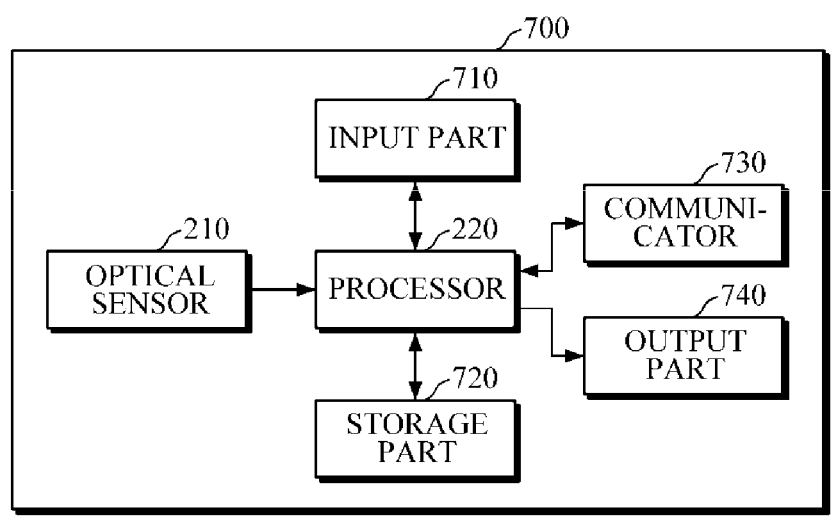
FIG. 7 is a block diagram illustrating an apparatus for measuring absorbance according to a second embodiment.

FIG. 7 is a block diagram illustrating another example of an apparatus for measuring absorbance. The apparatus of FIG. 7 is an apparatus capable of measuring absorbance of an object and may be embedded in an electronic device. In this case, examples of the electronic device may include a cellular phone, a smartphone, a tablet PC, a laptop computer, a personal digital assistant (PDA), a portable multimedia player (PMP), a navigation, an MP3 player, a digital camera, a wearable device, and the like. Examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, neither the electronic device nor the wearable device is limited to the listed examples.

Referring to FIG. 7, the apparatus 700 for measuring absorbance includes an optical sensor 210, a processor 220, an input part 710, a storage part 720, a communicator 730, and an output part 740. Here, the optical sensor 210 and the processor 220 are described above with reference to FIGS. 2 to 6, such that detailed description thereof will be omitted.

The input part 710 may receive input of various operation signals from a user. In one embodiment, the input part 710 may include a keypad, a dome switch, a touch pad (static pressure/capacitance), a jog wheel, a jog switch, a hardware (H/W) button, and the like. The touch pad, which forms a layer structure with a display, may be called a touch screen.

The storage part 720 may store programs or instructions for operation of the apparatus 700 for measuring absorbance, and the storage part 720 also may store data input to and output from the apparatus 700 for measuring absorbance. Further, the storage part 720 may store light quantity data of the first light and light quantity data of the second light, which are measured by the optical sensor 210, absorbance data of an object which is calculated by the processor 220, and the like.

The storage part 720 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, an optical disk, and the like. Further, the apparatus 700 for measuring absorbance may operate an external storage medium, such as web storage and the like, which performs a storage function of the storage part 720 on the Internet.

The communicator 730 may perform communication with an external device. For example, the communicator 730 may transmit, to the external device, data input by a user through the input part 710, the light quantity data of the first light and the light quantity data of the second light which are measured by the optical sensor 210, the absorbance data of an object which is calculated by the processor 220, and the like; or may receive, from the external device, various data used in obtaining absorbance data of an object.

In this case, the external device may be medical equipment using the data input by a user through the input part 710, the light quantity data of the first light and the light quantity data of the second light which are measured by the optical sensor 210, the absorbance data of an object which is calculated by the processor 220, and the like, a printer to print out results, or a display to display the results. In addition, the external device may be a digital TV, a desktop computer, a cellular phone, a smartphone, a tablet PC, a laptop computer, a personal digital assistant (PDA), a portable multimedia player (PMP), a navigation, an MP3 player, a digital camera, a wearable device, and the like, but the external device is not limited thereto.

The communicator 730 may communicate with an external device by using Bluetooth communication, Bluetooth Low Energy (BLE) communication, Near Field Communication (NFC), WLAN communication, Zigbee communication, Infrared Data Association (IrDA) communication, Wi- Fi Direct (WFD) communication, Ultra-Wideband (UWB) communication, Ant+ communication, WIFI communication, Radio Frequency Identification (RFID) communication, 3G communication, 4G communication, 5G communication, and the like. However, this list is an example and is not intended to be limiting.

The output part 740 may output the data input by a user through the input part 710, the light quantity data of the first light and the light quantity data of the second light which are measured by the optical sensor 210, the absorbance data of an object which is calculated by the processor 220, and the like. In one embodiment, the output part 740 may output the data input by a user through the input part 710, the light quantity data of the first light and the light quantity data of the second light which are measured by the optical sensor 210, the absorbance data of an object which is calculated by the processor 220, and the like, by using any one or any combination of an acoustic method, a visual method, and a tactile method. To this end, the output part 740 may include a display, a speaker, a vibrator, and the like.

Figure 8:
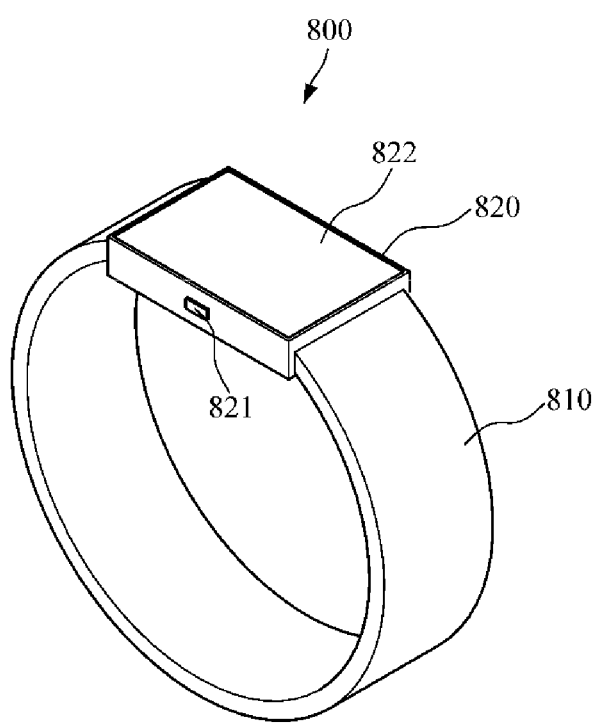
FIG. 8 is a perspective diagram of a wrist-type wearable device according to an embodiment.

FIG. 8 is a perspective diagram of a wrist-type wearable device according to an embodiment.

Referring to FIG. 8, the wrist-type wearable device 800 includes a strap 810 and a main body 820.

The strap 810 may be formed as a flexible band. However, this is an example, and the strap 810 is not limited thereto. That is, the strap 810 may be provided with various strap members which may be bent to be wrapped around a user's wrist.

The main body 820 may include the above-described optical sensors 300, 400, 500, and 600, or the apparatuses 200 and 700 for measuring absorbance. Further, the main body 820 may include a battery which supplies power to the wrist-type wearable device 800, the optical sensors 300, 400, 500, and 600, and the apparatuses 200 and 700 for measuring absorbance.

The wrist-type wearable device 800 may further include an input part 821 and a display 822 which are mounted in the main body 820. The input part 821 may receive input of various operation signals from a user. The display 822 may display data processed by the wrist-type wearable device 800, the optical sensors 300, 400, 500, and 600, and the apparatuses 200 and 700 for measuring absorbance, processing result data, and the like.

Figure 9:
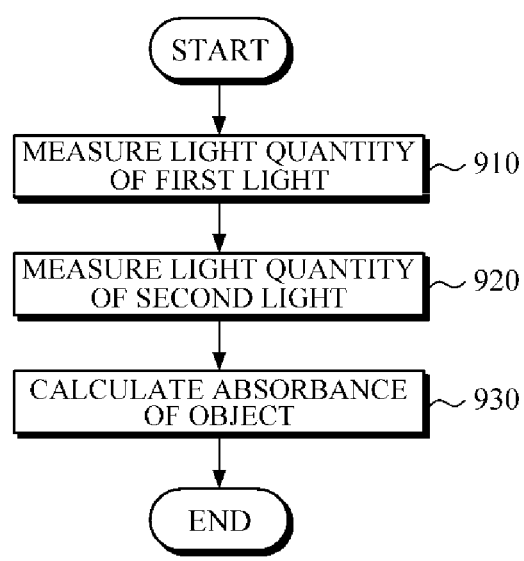
FIG. 9 is a flowchart illustrating an example of a method of measuring absorbance according to a first embodiment.

FIG. 9 is a flowchart illustrating an example of a method of measuring absorbance. The method of measuring absorbance of FIG. 9 may be performed by the apparatus 200 for measuring absorbance of FIG. 2.

Referring to FIGS. 2 and 9, the apparatus 200 for measuring absorbance may receive a first light which is emitted from a front surface of each light source and is reflected or scattered from an object, and may measure a light quantity of the received first light in 910.

The apparatus 200 for measuring absorbance may receive a second light, which is emitted from a rear surface of each light source and passes through holes of a substrate where light sources are mounted, and may measure a light quantity of the received second light in 920.

The apparatus 200 for measuring absorbance may calculate absorbance of an object based on the light quantity of the first light and the light quantity of the second light in 930. For example, the apparatus 200 for measuring absorbance may estimate an incident light quantity of light, which is emitted from a front surface of the light sources and is incident on an object, based on the light quantity of the second light. The absorbance of the object may be calculated by using Equation 1 based on the estimated incident light quantity and the light quantity of the first light. In another example, the apparatus 200 for measuring absorbance may calibrate the light quantity of the first light based on the light quantity of the second light by using a light quantity calibration equation (Equation 2) which defines a relationship between a change in the light quantity of the second light and the light quantity of the first light. The absorbance of the object may be calculated by using Equation 3 based on the calibrated light quantity of the first light.

Figure 10:
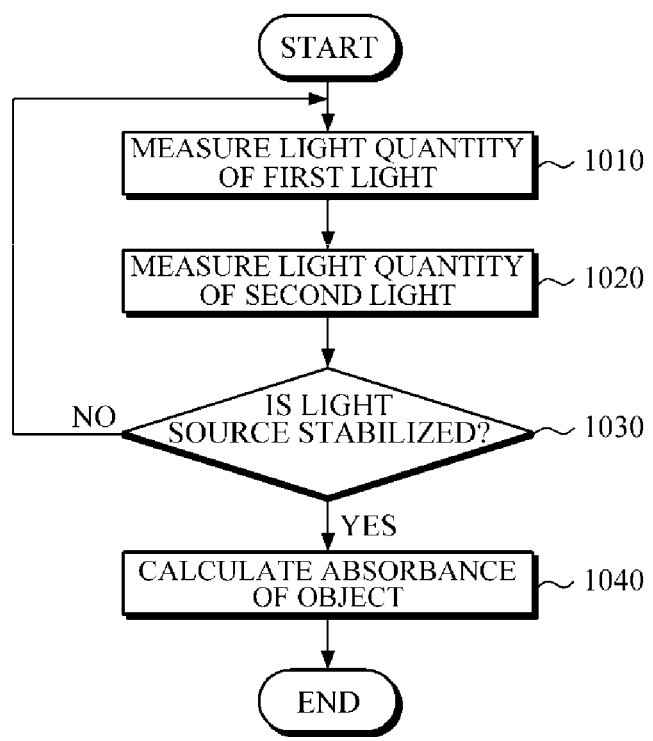
FIG. 10 is a flowchart illustrating a method of measuring absorbance according to a second embodiment.

FIG. 10 is a flowchart illustrating another example of a method of measuring absorbance. The method of measuring absorbance of FIG. 10 may be performed by the apparatus 200 for measuring absorbance of FIG. 2.

Referring to FIGS. 2 and 10, the apparatus 200 for measuring absorbance may receive a first light which is emitted from a front surface of each light source and is reflected or scattered from an object, and may measure a light quantity of the received first light in 1010.

The apparatus 200 for measuring absorbance may receive a second light which is emitted from a rear surface of each light source and passes through holes of a substrate where light sources are mounted, and may measure a light quantity of the received second light in 1020.

The apparatus 200 for measuring absorbance may determine whether the light sources are stabilized in 1030. In one embodiment, the apparatus 200 for measuring absorbance may determine whether the light sources are stabilized by using a coefficient of variation of the light quantity of the second light, a degree of wavelength shift of the light sources, a preset time, and the like. For example, the apparatus 200 for measuring absorbance may determine the stability of the light sources in response to a coefficient of variation of the light quantity of the second light being less than or equal to a predetermined first threshold value, in response to a degree of wavelength shift of the light sources. The degree of wavelength shift of the light may be calculated based on the light quantity of the second light, being less than or equal to a predetermined second threshold value, or in response to a lapse of time preset to operate the light sources.

Upon determining in 1030 that the light sources are stabilized, the apparatus 200 for measuring absorbance may calculate absorbance of an object based on the measured light quantity of the first light and the measured light quantity of the second light in 1040.

By contrast, upon determining in 1030 that the light sources are not stabilized, the apparatus 200 for measuring absorbance may return to 1010 to measure a light quantity of the first light.

This disclosure can be realized as a computer-readable code written on a computer-readable recording medium. Codes and code segments used for realizing the disclosure can be easily deduced by computer programmers of ordinary skill in the art. The computer-readable recording medium may be any type of recording device in which data is stored in a computer-readable manner. Examples of the computer-readable recording medium include a ROM, a RAM, a CD-ROM, a magnetic tape, a floppy disc, an optical disk, and the like. Further, the computer-readable recording medium can be distributed over a plurality of computer systems connected to a network so that a computer-readable recording medium is written thereto and executed therefrom in a decentralized manner.

Inventive concepts have been described herein with regard to embodiments. However, it will be obvious to those skilled in the art that various modifications can be made without departing from the gist of the embodiments. Therefore, it is to be understood that that the scope is not limited to the above-mentioned embodiments, but is intended to include various modifications and equivalents included within the spirit and scope of the appended claims.

What is claimed is:

1. An optical sensor comprising:
light sources configured to emit light;
a substrate on which the light sources are mounted, the substrate comprising holes in regions on which the light sources are mounted;
a first photodetector configured to receive a first light emitted from a front surface of each of the light sources, the first light being reflected or scattered from an object; and
at least one second photodetector configured to receive a second light emitted from a rear surface of each of the light sources, the second light passing through the holes corresponding to the light sources.

2. The optical sensor of claim 1, wherein the light sources are further configured to emit light of different wavelengths.

3. The optical sensor of claim 1, wherein a number of the at least one second photodetectors is equal to a number of the light sources, and
the at least one second photodetector corresponds to the light sources.

4. The optical sensor of claim 1, wherein a number of the at least one second photodetector is less than a number of the light sources.

5. The optical sensor of claim 1, wherein a number of the at least one second photodetector is one.

6. The optical sensor of claim 5, further comprising a light collector disposed between the substrate and the at least one second photodetector, and configured to collect the second light passed through the holes.

7. The optical sensor of claim 6, wherein the light collector comprises any one or any combination of a waveguide, a condensing lens, a reflection mirror, and a grating.

8. An apparatus for measuring absorbance, the apparatus comprising:
an optical sensor configured to:
receive a first light and a second light,
wherein the first light is reflected or scattered from an object, and
wherein the second light passes through holes of a substrate;
measure a first light quantity of the first light; and
measure a second light quantity of the second light; and
a processor configured to calculate an absorbance of the object, based on the first light quantity of the first light and the second light quantity of the second light.

9. The apparatus of claim 8, wherein the optical sensor comprises:
light sources configured to emit light;
the substrate on which the light sources are mounted, the substrate comprising the holes in regions on which the light sources are mounted;
a first photodetector configured to:
receive the first light emitted from a front surface of each of the light sources, the first light being reflected or scattered from the object; and
measure the first light quantity of the first light; and
at least one second photodetector configured to:
receive the second light emitted from a rear surface of each of the light sources, the second light passing through the holes corresponding to the light sources; and
measure the second light quantity of the second light.

10. The apparatus of claim 9, wherein the optical sensor further comprises a light collector disposed between the substrate and the at least one second photodetector, and configured to collect the second light passed through the holes.

11. The apparatus of claim 10, wherein the light collector comprises any one or any combination of a waveguide, a condensing lens, a reflection mirror, and a grating.

12. The apparatus of claim 9, wherein the processor is further configured to:
calibrate the first light quantity of the first light, based on a change in the second light quantity of the second light; and
calculate the absorbance of the object, using the first light quantity that is calibrated.

13. The apparatus of claim 12, wherein the processor is further configured to calibrate the first light quantity of the first light, using a light quantity calibration equation defining a relationship between the change in the second light quantity of the second light and the first light quantity of the first light.

14. The apparatus of claim 9, wherein the processor is further configured to:
determine whether the light sources are stabilized; and
based on the light sources being determined to be stabilized, calculate the absorbance of the object, based on the first light quantity of the first light and the second light quantity of the second light.

15. The apparatus of claim 14, wherein the processor is further configured to determine whether the light sources are stabilized based on any one or any combination of a coefficient of variation of the second light quantity of the second light, a degree of wavelength shift of the light sources, and a preset time.

16. A method of measuring absorbance, the method comprising:
receiving a first light that is emitted from a front surface of a light source and is reflected or scattered from an object;
measuring a first light quantity of the first light;
receiving a second light that is emitted from a rear surface of the light source and passes through a hole of a substrate on which the light source is mounted;
measuring a second light quantity of the second light; and
calculating absorbance of the object, based on the first light quantity of the first light and the second light quantity of the second light.

17. The method of claim 16, wherein the calculating the absorbance of the object comprises:
calibrating the first light quantity of the first light, based on a change in the second light quantity of the second light; and
calculating the absorbance of the object, using the first light quantity that is calibrated.

18. The method of claim 17, wherein the calibrating the first light quantity of the first light comprises calibrating the first light quantity of the first light, using a light quantity calibration equation defining a relationship between the change in the second light quantity of the second light and the first light quantity of the first light.

19. The method of claim 16, further comprising determining whether the light source is stabilized.

20. The method of claim 19, wherein the determining whether the light source is stabilized comprises determining whether the light source is stabilized, based on any one or any combination of a coefficient of variation of the second light quantity of the second light, a degree of wavelength shift of the light source, and a preset time.

21. The method of claim 19, wherein the calculating of absorbance of the object comprises, based on the light source being determined to be stabilized, calculating the absorbance of the object, based on the first light quantity of the first light and the second light quantity of the second light.

22. An optical sensor comprising:
light sources, each of the light sources being configured to:
  emit a first light from a first surface; and
  emit a second light from a second surface opposite to the first surface;
a first substrate comprising holes on which the second surface of each of the light sources is respectively disposed;
a first photodetector configured to receive the first light that is emitted from each of the light sources and that is reflected or scattered from an object;
one or more second photodetectors configured to receive the second light that is emitted from each of the light sources and that passes through each of the holes respectively corresponding to the light sources; and
a second substrate on which the one or more second photodetectors are mounted.

* * * * *